United States Patent

Axelsson et al.

[11] Patent Number: 5,314,903
[45] Date of Patent: May 24, 1994

[54] BENZIMIDAZOLE COMPOUNDS USEFUL AS CALCIUM CHANNEL BLOCKERS

[75] Inventors: Oskar Axelsson, Malmö; Mikkel Thaning, Hjärup, both of Sweden; Peter Moldt, Humlebaek, Denmark

[73] Assignee: NeuroSearch A/S, Glostrup, Denmark

[21] Appl. No.: 978,131

[22] Filed: Nov. 18, 1992

Related U.S. Application Data

[63] Continuation-in-part of Ser. No. 801,754, Dec. 3, 1991, abandoned.

[51] Int. Cl.$^5$ .................. A61K 31/415; C07D 235/30
[52] U.S. Cl. ........................ 514/388; 548/307.4; 548/306.1
[58] Field of Search .............. 548/307.4, 306.1; 514/388

[56] References Cited

U.S. PATENT DOCUMENTS 4,004,016  1/1977  Yale et al. ............. 548/306.1
5,210,091  5/1993  Axelsson et al. ........ 548/306.1

Primary Examiner—Joseph Paul Brust
Assistant Examiner—Mary Susan H. Gabilan
Attorney, Agent, or Firm—Gordon W. Hueschen

[57] ABSTRACT

The present invention discloses compounds of the formula

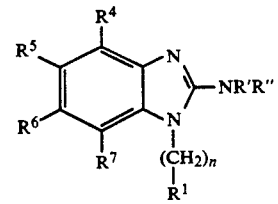

wherein
R' and R" independently of each other are hydrogen or alkyl, or R' and R" together form a 3 to 6 membered alkylene chain;
n is 1 or 2;
$R^1$ is phenyl which may be substituted one or more times with halogen, $CF_3$, alkoxy, alkyl, or amino; and
$R^4$, $R^5$, $R^6$ and $R^7$ independently of each other are hydrogen, halogen, amino, $CF_3$, alkyl or alkoxy; or a pharmaceutically-acceptable addition salt thereof.

The compounds are useful as pharmaceuticals, for example, in the treatment of ischemia, anoxia, migraine and psychosis.

7 Claims, No Drawings

BENZIMIDAZOLE COMPOUNDS USEFUL AS CALCIUM CHANNEL BLOCKERS

The present patent application is a continuation-in-part of copending U.S. patent application Ser. No. 07/801,754 which was filed on Dec. 3, 1991 now abandoned.

The present invention relates to therapeutical active compounds and their use as well as to pharmaceutical preparations comprising the compounds. The compounds of the invention possess valuable activity as calcium channel blockers which make them useful in the treatment of anoxia, ischemia, psychosis and migraine for example.

It is well known that an accumulation of calcium (calcium overload) in the brain is seen after anoxia, ischemia, migraine and other hyperactivity periods of the brain, such as after epileptic convulsions. An uncontrolled high concentration of calcium in the cells of the Central Nervous System (CNS) is known to cause most of the degenerative changes connected with the above diseases. Therefore compounds which can block the calcium channels of brain cells will be useful in the treatment of anoxia, ischemia, migraine, epilepsia and in the prevention of the degenerative changes connected with the same.

Compounds blocking the so-called L-type calcium channels in the CNS will be useful for the treatment of the above disorders by directly blocking the calcium uptake in the CNS.

Further, it is well known that the so called N- and P-types of calcium channels are involved in the regulation of neurotransmitter release. Compounds blocking the N- and/or P-types of calcium channels will indirectly and very powerfully prevent calcium overload in the CNS after the hyperactivity periods of the brain as described above by inhibiting the enhanced neurotransmitter release seen after such hyperactivity periods of the CNS, and especially the neurotoxic enhanced neurotransmitter, glutamate, release after such hyperactivity periods of the CNS. Furthermore, blockers of the N- and/or P-types of calcium channels will as dependent upon the selectivity of the compound in question inhibit the release of various other neurotransmitters such as aspartate, GABA, glycine, dopamine, serotonin and noradrenaline. Therefore blockers of N- and/or P-types of calcium channels may be useful in the treatment of psychosis, Parkinsonism, depression, epilepsia and other convulsive disorders.

Yale et al in U.S. Pat. No. 4,004,016 discloses related compounds having claimed antiinflammatory activity. No biological details appear from this patent.

It is an object of the present invention to provide compounds capable of blocking the L-type and/or the N-type and/or the P-type of calcium channels.

The invention then, inter alia, comprises the following, alone or in combination.

A method of treating a disorder, which is responsive to the blockade, partly or completely, of calcium channels of the central nervous system, of a mammal, including a human, which comprises administering to a patient in need thereof a therapeutically-effective amount of a compound having the formula:

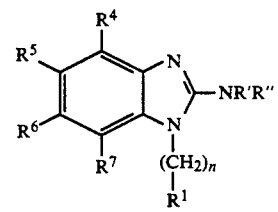

wherein
R' and R" independently of each other are hydrogen or alkyl, or R' and R" together form a 3 to 6 membered alkylene chain;
n is 1 or 2;
$R^1$ is phenyl which may be substituted one or more times with halogen, $CF_3$, alkoxy, alkyl, or amino; and
$R^4$, $R^5$, $R^6$ and $R^7$ independently of each other are hydrogen, halogen, amino, $CF_3$, alkyl or alkoxy; or a pharmaceutically-acceptable addition salt thereof;

and a method as above, wherein anoxia, ischemia, migraine, psychosis, or epilepsia is treated;

and a method as above, wherein psychosis, Parkinsonism, depression, epilepsia or other convulsive disorders is treated;

further a method of preventing the degenerative changes connected with anoxia, ischemia, migraine, and epilepsia, which comprises administering to a patient in need thereof a therapeutically-effective amount of a compound having the formula:

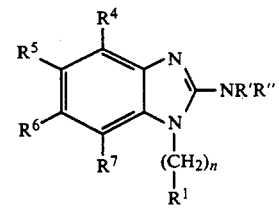

wherein
R' and R" independently of each other are hydrogen or alkyl, R' and R" together form a 3 to 6 membered alkylene chain;
n is 1 or 2;
$R^1$ is phenyl which may be substituted one or more times with halogen, $CF_3$, alkoxy, alkyl, or amino; and
$R^4$, $R^5$, $R^6$ and $R^7$ independently of each other are hydrogen, halogen, amino, $CF_3$, alkyl or alkoxy; or a pharmaceutically-acceptable addition salt thereof, and the method as any above, wherein the compound employed is 2-Amino-1-(4-chlorobenzyl)-5-trifluoromethylbenzimidazole or a pharmaceutically-acceptable addition salt thereof;

and the method as any above, wherein the compound employed is
2-Amino-1-(4-chlorobenzyl)-benzimidazole,
2-Amino-1-(4-methylbenzyl)-5-trifluoromethylbenzimidazole,
2-Amino-1-(4-methoxybenzyl)-5-trifluoromethylbenzimidazole,
2-Dimethylamino-1-(4-chlorobenzyl)-5-trifluoromethylbenzimidazole, or
2-Amino-1-(4-dimethylaminobenzyl)-5-trifluoromethylbenzimidazole or a pharmaceutically-acceptable addition salt thereof;

and the method as any above, wherein the active ingredient is administered in the form of a pharmaceutical composition thereof, in which it is present together with a pharmaceutically-acceptable carrier of diluent;

further a compound having the formula

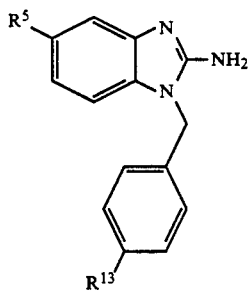

wherein
$R^5$ is chloro, amino, $CF_3$, alkyl or alkoxy; and
$R^{13}$ is chloro, amino, alkyl, or alkoxy, or a pharmaceutically acceptable salt thereof;
and a compound as above which is
2-Amino-1-(4-methylbenzyl)-5-trifluoromethylbenzimidazole,
2-Amino-1-(4-methoxybenzyl)-5-trifluoromethylbenzimidazole,
2-Dimethylamino-1-(4-chlorobenzyl)-5-trifluoromethylbenzimidazole, or
2-Amino-1-(4-dimethylaminobenzyl)-5-trifluoromethylbenzimidazole or a pharmaceutically-acceptable addition salt thereof;
and a compound as above which is 2-Amino-1-(4-chlorobenzyl)-5-trifluoromethylbenzimidazole or a pharmaceutically-acceptable addition salt thereof,
and furthermore a pharmaceutical composition for the treatment of a disorder of a mammal, including a human, which disorder is responsive to the blockade, partly or completely, of the calcium channels of the central nervous system, comprising an effective amount of a compound as any above, or a pharmaceutically-acceptable addition salt thereof, together with at least one pharmaceutically-acceptable carrier or diluent.

Preferred compounds according to the present invention are those which are substituted at $R^5$ and $R^{13}$ as described above, wherein both of $R^5$ and $R^{13}$ are different from hydrogen.

More preferred compound are those wherein $R^5$ is chloro, amino, $CF_3$, alkyl or alkoxy and, simultaneously, $R^{13}$ is chloro, amino, alkoxy or alkyl.

The most preferred compound according to the present invention is 2-amino-1-(4-chlorobenzyl)-5-trifluoromethylbenzimidazole.

Examples of pharmaceutically-acceptable addition salts include inorganic and organic acid addition salts such as the hydrochloride, hydrobromide, phosphate, sulphate, citrate, lactate, tartrate, maleate, fumarate, mandelate, oxalate, benzoate, ascorbate, cinnamate and the acetate.

Halogen is fluorine, chlorine, bromine, or iodine; chlorine and bromine are preferred groups.

Alkyl means a straight chained or branched chain of from one to six carbon atoms or cyclic alkyl of from three to seven carbon atoms, including but not limited to, methyl, ethyl, propyl, isopropyl, butyl, isobutyl, t-butyl, pentyl, hexyl, cyclopropyl, cyclobutyl, cyclopentyl, cyclohexyl; methyl, ethyl, propyl and isopropyl are preferred groups.

Alkoxy is O-alkyl, wherein alkyl is as defined above.
Amino is $NH_2$ or NH-alkyl or N-(alkyl)$_2$, wherein alkyl is as defined above.

The compounds can be prepared by conventional methods well known in the art. Such methods include the step of reacting a compound having the formula

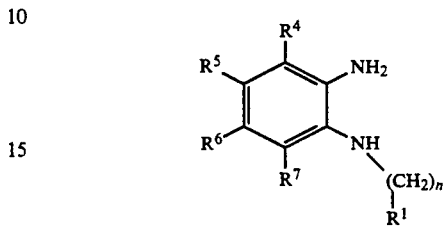

wherein n, $R^1$, $R^4$, $R^5$, $R^6$ and $R^7$ have the meanings set forth above, with BrCN to form a compound of the invention, and if the 2-amino group of the end product is intended to be alkyl substituted, then by a following alkylation with the relevant alkylhalogenide or another suitable alkylating reagent.

The starting compounds are well known compounds, either as commercial available compounds, or easily available according published literature.

BIOLOGY

A high influx of calcium from extracelluar compartments into neurons is seen after opening of voltage operated calcium channels. Such opening of calcium channels may be induced by depolarization of neuronal membranes.

A crude synaptosome preparation contains small vesicles surrounded by neuronal membranes, and it is possible to study an opening of the voltage operated calcium channels in such a preparation.

In the below described test influx of $^{45}Ca$ into rat synaptosomes is studied under depolarized conditions. The effect of test substances on the depolarization induced calcium uptake can thus be studied.

The calcium influx measured in this test is believed to represent the P- and L-type of calcium channels and compounds believed to block both the P- and the L-type of calcium channels will often exhibit a bifasic dose/response curve. The compounds of the present invention which potently block the calcium influx of up to 20 to 40% in this test are believed to be blockers of predominantly the P-type of calcium channels and the compounds of the present invention, which at somewhat higher concentrations block the calcium influx more completely or totally, are believed to be both P- and L-type calcium channel blockers, or predominantly L-type of calcium channel blockers.

Test Procedure

The cerebral cortex from a male Wistar rat is homogenized in 20 ml ice cold 0.32M saccharose. In the following steps the temperature is kept at 0° C. to 4° C. The homogenate is centrifuged at 1,000×g for 10 minutes and the supernatant recentrifuged for 20 minutes at 18,000×g. The obtained pellet is resuspended in 0.32M saccharose (10 ml per g of original tissue).

Aliquots of 0.05 ml of the hereby obtained synaptosome suspension are added to glass tubes containing 0.625 ml of a NaCl buffer (136 mM NaCl, 4 mM KCl, 0.35 mM $CaCl_2$, 1.2 mM $MgCl_2$, 20 mM Tris HCl, 12 mM glucose, pH 7.4) as well as 0.025 ml of different test substances in 48% ethanol. These tubes are pre-incubated for 30 minutes on ice and thereafter for 6 minutes at 37° C.

$^{45}$Ca uptake is initiated by addition to above glass-tubes of 0.4 ml $^{45}$CaCl$_2$ (specific activity: 29-39 Ci/g; 0.5 Ci per tube). For depolarized samples the 0.4 ml $^{45}$CaCl$_2$ contain KCl (145 mM) and for non-depolarized NaCl (145 mM). The samples are incubated for 15 seconds.

The $^{45}$Ca uptake is stopped by filtering through glass fibre filters, which are subsequently washed 3 times with an ice cold solution of 145 mM KCl, 7 mM EGTA and 20 mM Tris HCl, pH 7.4 (5.0 ml). The radioactivity on the filters are measured by liquid scintillation spectrometry. Experiments are performed in duplicate.

Sample preparation

Above test substances are dissolved in, for example, 10 ml 48% ethanol at a concentration of 0.44 mg/ml. Dilutions are made in ethanol. Test substances are tested at concentrations of 0.1, 0.3, 1, 3, 10 ... μg/ml.

Results

Generally the compounds of the present invention in a low micromolar range (0.5 to 2 μM) block 20 to 40% of the calcium influx measured in the above described test. Examples of such compounds are compounds 1F, 1M and 1O, as described herein. Other compounds of the present invention also show the characteristics of L-type calcium channel blocking properties at somewhat higher concentrations.

It has been found (electrophysiological studies using the patch-clamp technique as described by Hamill et al., Pflügers Arch. 391, 85-100 (1981)), that compounds of the invention block the N-type of calcium channels in a low micromolar range (1 to 20 μM). Some compounds of the invention also block the L-type calcium channels.

Therefore the compounds are useful in the treatment of anoxia, ischemia and migraine (see also WO 91/07980).

Further it has been found that the compounds of the invention, for example 1-(4-chlorobenzyll)-5-trifluoromethyl-2-amino-benzimidazole potently (3 mg/kg) antagonize hypermotility in mice as induced by amphetamine. This is in full accordance with the influence of N- and P-type calcium channel blockers on transmitter release in the central nervous system. Therefore the compounds of the invention are useful as antipsychotics for example.

PHARMACEUTICAL COMPOSITIONS

The compounds of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Tablets containing ten (10) milligrams of active ingredient or, more broadly, one (1) to one hundred (100) milligrams, per tablet, are accordingly suitable representative unit dosage forms.

METHOD OF TREATING

Due to the high degree of activity, the compounds of the invention may be administered to a subject, e.g., a living animal body, in need of alleviation, treatment, or amelioration of a disorder which is responsive to the activity or influence of the compounds of the present invention including responsive to the Ca overload blocking properties of the compounds of the invention. The compounds of the invention are preferably administered in the form of an acid addition salt thereof, concurrently, simultaneously, or together with a pharmaceutically-acceptable carrier or diluent, especially and preferably in the form of a pharmaceutical composition thereof, whether oral, rectal, or parenteral (including subcutaneous) route, in an effective amount. Suitable dosage ranges are 1-500 milligrams daily, preferably 1-100 milligrams daily, and especially 1-30 milligrams daily, depending as usual upon the exact mode of administration, form in which administered, the indication toward which the administration is directed, the subject involved and the body weight of the subject involved, and the preferences and experience of the physician or veterinarian in charge.

The following examples will illustrate the invention further; however they are not to be construed as limiting.

EXAMPLE 1

2-Amino-1-(4-chlorobenzyl)-5-trifluoromethylbenzimidazole. To an ice cooled solution of 2-(4-chlorobenzylamino)-5-trifluoromethylaniline hydrochloride (6.74 g, 20 mmol) in DMF (100 ml) and triethylamine (2.8 ml) was added cyanogen bromide (2.75 g, 26 mmol). The ice bath was removed after two hours and the mixture was stirred overnight at room temperature. The reaction mixture was diluted with water and neutralized with an aqueous solution of sodium carbonate (5%). The product was filtered off and purified with activated charcoal and crystallization from ethanol. Yield 2.93 g (45%).

EXAMPLE 2

2-(4-Chlorobenzylamino)-5-trifluoromethylaniline hydrochloride. A solution of 2-(4-chlorobenzylamino)-5-trifluoromethylnitrobenzene (70 g, 0.21 mmol) in ethanol (500 ml) was hydrogenated at a pressure of 4 bar. When the reaction was finished the product was filtered through a plug of celite into a flask containing 25 ml conc. HCl. After evaporation the product was suspended in petrol ether and filtered off. Yield 57 g.

EXAMPLE 3

2-(4-Chlorobenzylamino)-5-trifluoromethylnitrobenzene. A mixture of 4-chloro-3-nitrobensotriflouride (159 g, 0.7 mol), 4-chlorobenzylamine (100 g, 0.7 mol) and potassium carbonate (110 g, 0.8 mol) in DMF (500 ml) was slowly heated to 80° C. and kept at that temperature for 3 h. The reaction mixture was allowed to cool and diluted with water to a volume of 4 l. The product was filtered off, rinsed with water and sucked dry. The crystals were then suspended in petrol ether (400 ml) and stirred for 1 h. Filtration and drying gave the product in a yield of 209 g (90%).

EXAMPLE 4

2-Amino-1-(4-chlorobenzyl)-benzimidazole. A mixture of 2-amino benzimidazole (6.66 g, 50 mmol), 4-chlorobenzylchloride (8.86 g, 55 mmol), and potassium carbonate (13.8 g, 100 mmol) in DMF (150 ml) was heated to 50° C. overnight. After dilution with water the product was filtered off. Recrystallization from water/ethanol 1:2 gave pure product. Yield 5.6 g (46%) mp 196°-197° C.

EXAMPLE 5

1-Benzyl-2-(1-piperidyl)-benzimidazole. A mixture of 1-benzylbenzimidazol-2-one (1.0 g, 4.4 mmol) and POCl₃ (10 ml) was refluxed for two hours. Dilution with ice/water was followed by extraction with ethyl acetate, drying (MgSO4) and evaporation left a yellow oil to which was added piperidine (10 ml) and toluene (15 ml). This mixture was refluxed for 5 days. Water and more toluene was added and the phases were separated. The organic phase was washed twice with water and the product was transferred to 4M HCl, washed with ethyl acetate, made basic by the addition of 4M aqueous NaOH, taken up in methylene chloride, dried and evaporated. The product was then purified by chromatography on silica gel with methylene chloride+4% ethanol as the eluent. Yield 150 mg. Mp. 84°-87° C.

EXAMPLE 6

1-(4-Chlorobenzyl)-2-dimethylamino-5-trifluoromethylbenzimidazole. A mixture of 2-amino-1-(4-chlorobenzyl)-5-trifluoromethylbenzimidazole (1.0 g, 3.07 mmol), methyl iodide (4.35 g, 30.7 mmol), and potassium carbonate (0.93 g, 6.75 mmol) in methanol (20 ml) was refluxed for one week. The methanol was removed in vacuum and the product was taken up in ethyl acetate. Washing with water was followed by drying and evaporation and the product was purified by column chromatography on silica gel with methylene chloride/methanol 9:1 as the eluent. Mp 103-107° C.

TABLE 1

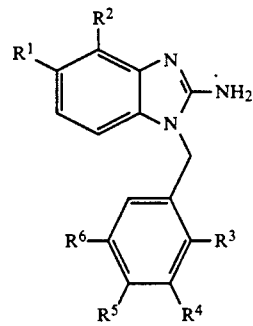

| No. | R1 | R2 | R3 | R4 | R5 | R6 | mp/°C. | Starting material |
|---|---|---|---|---|---|---|---|---|
| 1A | CF3 | H | H | H | H | H | 209-215 | 2A |
| 1B | CF3 | H | H | H | Cl | H | 209-213 | 2B |
| 1C | CF3 | H | OCH3 | H | H | Cl | 206-210 | 2C |
| 1D | CF3 | H | H | Cl | H | H | 236-238 | 2D |
| 1E | CF3 | H | H | H | t-Bu | H | 241-242 | 2E |
| 1F | CF3 | H | H | H | CF3 | H | 254-255 | 2F |
| 1G | CF3 | H | Cl | H | Cl | H | 192-195 | 2G |
| 1H | CF3 | H | H | Cl | Cl | H | 253-255 | 2H |
| 1I | CF3 | H | H | CF3 | H | CF3 | 196-198 | 2I |
| 1J | OCH3 | H | H | H | Cl | H | 202-204 | 2J |
| 1K | CF3 | H | H | H | Br | H | 234-235 | 2K |
| 1L | CF3 | H | H | H | F | H | 237-238 | 2L |
| 1M | CF3 | H | H | H | CH3 | H | 194-196 | 2M |
| 1N | CF3 | H | H | H | OCH3 | H | 205-206 | 2N |
| 1O | CF3 | H | H | H | N(CH3)2 | H | 184-186 | 2O |
| 1P | H | CF3 | H | H | Cl | H | 209-211 | * |
| 1Q | H | H | H | H | Cl | H | 196-197 | * |

Compounds 1A-1O were prepared according to example 1. 1P and 1Q were prepared according to example 4.

TABLE 2

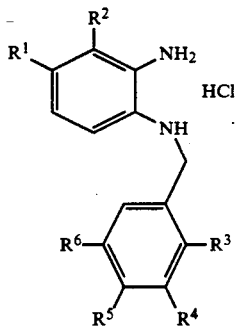

| No. | R1 | R2 | R3 | R4 | R5 | R6 | mp/°C. | Starting material |
|---|---|---|---|---|---|---|---|---|
| 2A | CF3 | H | H | H | H | H | 160–172(d) | 3A |
| 2B | CF3 | H | H | H | Cl | H | 165–174(d) | 3B |
| 2C | CF3 | H | OCH3 | H | H | Cl | 177–190(d) | 3C |
| 2D | CF3 | H | H | Cl | H | H | 176–178 | 3D |
| 2E | CF3 | H | H | H | t-Bu | H | 174–178 | 3E |
| 2F | CF3 | H | H | H | CF3 | H | 164–167 | 3F |
| 2G | CF3 | H | Cl | H | Cl | H | 150–170(d) | 3G |
| 2H | CF3 | H | H | Cl | Cl | H | >250 | 3H |
| 2I | CF3 | H | H | CF3 | H | CF3 | 173–176 | 3I |
| 2J | OCH3 | H | H | H | Cl | H | oil | 3J |
| 2K | CF3 | H | H | H | Br | H | 135–136 | 3K |
| 2L | CF3 | H | H | H | F | H | 113–115 | 3L |
| 2M | CF3 | H | H | H | CH3 | H | 135–137 | 3M |
| 2N | CF3 | H | H | H | OCH3 | H | 110–112 | 3N |
| 2O | CF3 | H | H | H | NMe2 | H | 160–162 | 3O |

Compounds 2A–2O were prepared according to example 2.

TABLE 3

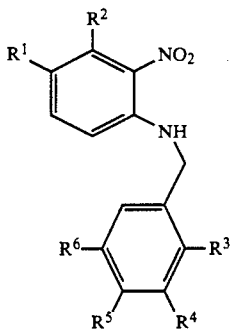

| No. | R1 | R2 | R3 | R4 | R5 | R6 | mp/°C. |
|---|---|---|---|---|---|---|---|
| 3A | CF3 | H | H | H | H | H | 80–81 |
| 3B | CF3 | H | H | H | Cl | H | 71–76 |
| 3C | CF3 | H | OCH3 | H | H | Cl | 118–126 |
| 3D | CF3 | H | H | Cl | H | H | 78–81 |
| 3E | CF3 | H | H | H | t-Bu | H | oil |
| 3F | CF3 | H | H | H | CF3 | H | 69–71 |
| 3G | CF3 | H | Cl | H | Cl | H | 93–96 |
| 3H | CF3 | H | H | Cl | Cl | H | 94–95 |
| 3I | CF3 | H | H | CF3 | H | CF3 | 137–140 |
| 3J | OCH3 | H | H | H | Cl | H | 140–142 |
| 3K | CF3 | H | H | H | Br | H | 90–93 |
| 3L | CF3 | H | H | H | F | H | 95–97 |
| 3M | CF3 | H | H | H | CH3 | H | 87–88 |
| 3N | CF3 | H | H | H | OCH3 | H | 58–62 |
| 3O | CF3 | H | H | H | NMe2 | H | 158–160 |

Compounds 3A–3O were prepared according to example 3.

We claim:

1. A method of treating a disorder, which is responsive to the partial or complete blockade of calcium channels of the central nervous system, of a mammal, including a human, which comprises administering to a mammal in need thereof a therapeutically-effective amount of a compound selected from those having the formula:

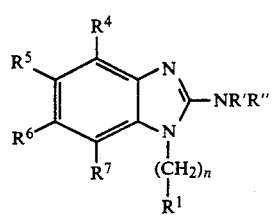

wherein
R' and R" independently of each other are hydrogen or alkyl, or R' and R" together form a 3 to 6 membered alkylene chain;
n is 1 or 2;
$R^1$ is phenyl which may be substituted one or more times with halogen, $CF_3$, alkoxy, alkyl, or amino; and
$R^4$, $R^5$, $R^6$ and $R^7$ independently of each other are hydrogen, halogen, amino, $CF_3$, alkyl or alkoxy; or a pharmaceutically-acceptable addition salt thereof.

2. A method as in claim 1, wherein anoxia, ischemia, migraine, psychosis, or epilepsia is treated.

3. A method as in claim 1, wherein psychosis, Parkinsonism, depression, epilepsia or other convulsive disorder is treated.

4. A method of claim 1, wherein the compound employed is 2-Amino-1-(4-chlorobenzyl)-5-trifluoromethylbenzimidazole or a pharmaceutically-acceptable addition salt thereof.

5. A method of claim 1, wherein the compound employed is
2-Amino-1-(4-chlorobenzyl)-benzimidazole, 2-Amino-1-(4-methylbenzyl)-5-trifluoromethylbenzimidazole, 2-Amino-1-(4-methoxybenzyl)-5-trifluoromethylbenzimidazole, 2-Dimethylamino-1-(4-chlorobenzyl)-5-trifluoromethylbenzimidazole, or 2-Amino-1-(4-dimethylaminobenzyl)-5-trifluoromethylbenzimidazole, or a pharmaceutically-acceptable addition salt of any of the foregoing compounds.

6. A method of claim 1, wherein the active ingredient is administered in the form of a pharmaceutical composition thereof, in which it is present together with a pharmaceutically-acceptable carrier or diluent.

7. A method of preventing degenerative changes connected with anoxia, ischemia, migraine, and epilepsia, which comprises administering to a patient in need thereof a therapeutically-effective amount of a compound selected from those having the formula:

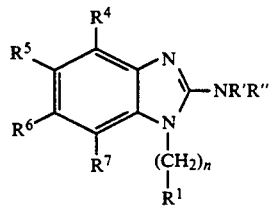

wherein
  R' and R" independently of each other are hydrogen or alkyl, or R' and R" together form a 3 to 6 membered alkylene chain;
  n is 1 or 2;
  $R^1$ is phenyl which may be substituted one or more times with halogen, $CF_3$, alkoxy, alkyl, or amino; and
  $R^4$, $R^5$, $R^6$ and $R^7$ independently of each other are hydrogen, halogen, amino, $CF_3$, alkyl or alkoxy; or a pharmaceutically-acceptable addition salt thereof.

* * * * *